United States Patent [19]
Böcker et al.

[11] Patent Number: 5,427,672
[45] Date of Patent: Jun. 27, 1995

[54] PLANAR SENSOR MADE OF CERAMIC MATERIAL, FOR DETECTING COMBUSTIBLE GASES

[75] Inventors: Wolfgang Böcker, Eppstein/Taunus; Christine Köstler, Bad Soden am Taunus; Hermann Moser, Darmstadt; Andreas Roosen, Hofheim/Taunus, all of Germany

[73] Assignee: Hoechst Aktiengesellschaft, Frankfurt am Main, Germany

[21] Appl. No.: 101,234

[22] Filed: Aug. 2, 1993

[30] Foreign Application Priority Data

Jul. 31, 1992 [DE] Germany .......... 42 25 279.2

[51] Int. Cl.⁶ .......... G01N 27/26
[52] U.S. Cl. .......... 204/426; 204/425; 204/429
[58] Field of Search .......... 204/424, 425, 426, 427, 204/428, 429

[56] References Cited

U.S. PATENT DOCUMENTS

| | | | |
|---|---|---|---|
| 4,798,693 | 1/1989 | Mase et al. | 204/426 |
| 5,108,577 | 4/1992 | Mase et al. | 204/426 |
| 5,139,829 | 8/1992 | Minoha et al. | 427/123 |

FOREIGN PATENT DOCUMENTS

| | | |
|---|---|---|
| 0203351 | 12/1986 | European Pat. Off. . |
| 0331050 | 9/1989 | European Pat. Off. . |
| 0390337 | 10/1990 | European Pat. Off. . |
| 0466020 | 1/1992 | European Pat. Off. . |
| 0468500 | 1/1992 | European Pat. Off. . |
| 0512500 | 11/1992 | European Pat. Off. . |
| 3537709C2 | 4/1986 | Germany . |
| 3942384 | 6/1990 | Germany . |
| 4021929 | 1/1992 | Germany . |

Primary Examiner—John Niebling
Assistant Examiner—Bruce F. Bell
Attorney, Agent, or Firm—Foley & Lardner

[57] ABSTRACT

A planar sensor made of ceramic material, for measuring and detecting combustible gases and/or the oxygen content in furnaces or in the exhaust gases of internal combustion engines, is described. The sensor has an at least five-layered structure on the basis of a combination of three zirconium dioxide layers with two aluminum oxide layers, a metallic heating resistor being embedded between two aluminum oxide layers, and three zirconium dioxide layers being combined with two platinum electrodes and one further electrode made of a binary or ternary alloy of platinum with gold, nickel, copper, rhodium, ruthenium, palladium or titanium. A process for fabricating the sensor is also described. It is also possible for the sensor to be combined, according to the invention, with a suitable housing which on its outside is provided with connecting wires and plugs for transmitting the measured signals.

13 Claims, 2 Drawing Sheets

PLANAR SENSOR MADE OF CERAMIC MATERIAL, FOR DETECTING COMBUSTIBLE GASES

FIELD OF THE INVENTION

The present invention relates to a planar sensor made of ceramic material, which—incorporated in a housing—can be used for measuring and detecting combustible gases and/or the oxygen content in furnaces or in the exhaust gases of internal combustion engines. The invention further relates to a process for fabricating a planar sensor of this type, starting from ceramic tapes on the basis of zirconium dioxide.

DESCRIPTION OF RELATED ART

The use of catalysts which are suitable for the effective decomposition of noxious gases such as carbon monoxide, nitrogen oxides or unoxidized or only partially oxidized hydrocarbons contained in the combustion exhaust gases of internal combustion engines and furnaces, has initiated a new era in motor vehicle manufacture. Day-to-day practice has shown, however, that the catalysts, which theoretically should meet their intended objective satisfactorily for decades, nevertheless are sometimes subject to a not inconsiderable ageing process. After a service life which varies from case to case, the so-called conversion efficiency of the catalyst is reduced and thus leads to an unwanted increased emission of pollutants which affects the environment. In order to minimize this unnecessary release of pollutants, the exhaust gases must remain subject to continuous testing even after they have left the catalyst.

German Published Specification 40 21 929 has disclosed a sensor which can be placed downstream of the catalyst in motor vehicles and which is suitable for determining the proportion of hydrogen in combustion exhaust gases, especially if oxygen is present at the same time. The known sensor is also described in a planar embodiment.

This sensor has the drawback, however, that the individual proportions of each of the various pollutant gases in the overall mixture cannot be indicated in an unambiguously differentiating manner.

SUMMARY OF THE INVENTION

The object of the invention is therefore to provide a miniaturized sensor, especially one having a planar construction, which is universally suitable for the continuous determination not only of oxygen but also of combustible gases in combustion exhaust gases of variable composition and temperature, and which enables quantitative determination of the individual proportions of the gaseous components in the overall mixture.

This object is achieved by a sensor of the generic type as mentioned in the introduction, which sensor is distinguished in that it has an at least five-layered structure on the basis of a combination of three zirconium dioxide layers with two aluminum oxide layers, a metallic heating resistor being embedded between two aluminum oxide layers, and three zirconium dioxide layers being combined with two platinum electrodes and one further electrode made of a binary or ternary alloy of platinum with gold, nickel, copper, rhodium, ruthenium, palladium or titanium.

DETAILED DESCRIPTION

The zirconium dioxide composition may additionally comprise inorganic dopants. Possible inorganic dopants are CaO, MgO, CeO and $Y_2O_3$. The zirconium dioxide composition is preferably doped with $Y_2O_3$. In this manner, a large number of vacant sites is generated for $O^{2-}$ ions, which make the ceramic ionically conductive. In the range of from 3.5 to 14.0% by weight of $Y_2O_3$, preferably of from 5 to 10% by weight, based on the total amount of zirconium dioxide composition, the ionic conductivity is particularly suitable for the intended use of the sensor downstream of the catalyst. The correct choice of the Y content also improves the stability of the sensor against thermal shock. Oxide mixtures comprising 5% by weight of $Y_2O_3$ produce purely tetragonal grains during sintering. Mixtures comprising 10% by weight of $Y_2O_3$ produce a mixture of tetragonal and cubic grains. In both cases, a so-called internal work hardening inhibits or entirely prevents unwanted spreading of cracks in the ceramic. The use of a zirconium dioxide comprising $Y_2O_3$ is known, inter alia, from German Patent 35 37 709.

According to the invention, the zirconium dioxide layers are arranged in such a way that, on a first layer, an electrode made of platinum is arranged which is applied in the form of a paste comprising the metal as a finely particulate powder together with organic binders and, if required, solvent. On the first layer with the electrode made of platinum a second layer made of zirconium dioxide is arranged which has a central cutout, which in turn has a connection to an external edge of the layer. The termination is formed by a third layer made of zirconium-dioxide, which, on its surface which faces away from the second layer having the cutout, carries two electrodes which are preferably arranged parallel and which are made of platinum and of a platinum alloy. The electrodes of the third layer are likewise preferably applied in the form of pastes which comprise platinum, or the alloy, as a finely particulate powder, together with organic binders and additionally, if required, solvent. The electrodes may, however, alternatively be applied by other conventional methods, for example by sputtering, by electrodeposition or according to the chemical vapor deposition method, in which previously formed volatile precursors are carried to the substrate surface and are decomposed there.

The layer thicknesses of the individual zirconium dioxide layers can be different and are in the range of from 0.2 to 2.0 mm, preferably of from 0.5 to 1.1 mm, particularly preferably of from 0.5 to 0.9 mm.

On that side of the three-layer combination of zirconium dioxide layers which does not carry any electrodes, the electric heating element comprising two aluminum layers and an electric heating resistor is arranged according to the invention. The heating element permits a reliable determination of the combustion exhaust gases by the zirconium dioxide sensor element even when these are still cold or have not yet reached a particular operating temperature. The heating element has a layered structure, the electric heating resistor having a preferably meander-like course in the interior of the electrically insulating ceramic made of $Al_2O_3$ and being constructed from a suitable refractory metal of low conductivity (e.g. tungsten). Two contacts pointing outwards allow the electric heating resistor to be connected to a power source. Expediently, the heating element is connected, via a temperature-dependent resistor, in such a way that at elevated temperatures of the combustion exhaust gases to be measured the heating output of the heating element is reduced.

The heating element can be connected mechanically (e.g. by a clamping mechanism or a pressure spring) to the actual sensor composed of zirconium dioxide layers and electrodes.

For use, the sensor is usually installed in a suitable housing in such a manner that the layer planes are parallel to the axis of the housing. The housing can expediently be constructed from corrosion-resistant metal, for example from high-grade steel, the interior of the housing being subdivided into two chambers in a gas-tight manner by a ceramic element, one of which chambers is in direct contact with the combustion exhaust gases, the other chamber being insulated against the combustion exhaust gases. The zirconium dioxide sensor element according to the invention is arranged in such a way that the free electrodes are located in the chamber containing the combustion exhaust gases, while the voltage pick-off takes place in the insulated chamber. The voltage pick-off itself should be carried out in an isolated circuit in order to minimize the number of possible error sources during the measurement. The housing is provided on its outside with connecting wires and plugs to make it suitable for fitting in internal combustion engines of motor vehicles or in combustion plants. The geometric dimensions of the areal sensor can be chosen at will. For example, it may be rectangular, square or round. Because of its suitability for fitting, an approximately elongated, rectangular shape is preferred. The overall thickness of the sensor is preferably approximately from 2 to 6 mm. The external dimensions are preferably 10×50 mm.

It has been found, surprisingly, that the construction according to the invention of the sensor, in spite of its simplicity, enables quantitative detection of the most important individual components of a mixture of combustion exhaust gases. According to the functional principle of the determination, the partial pressure of an individual component is first registered by means of the voltage difference between the reference electrode inside the sensor and a first measuring electrode. This signal is related to the voltage difference between the reference electrode and the second measuring electrode. Owing to the different chemical compositions of the two measuring electrodes, the individual signals allow inferences regarding different subcombinations of individual components of the overall mixture and, according to the abstraction principle, produce values for the individual components themselves. If yet more individual components were required to be determined, it may be expedient to provide yet a third measuring electrode having a different chemical composition on the sensor according to the invention.

The invention further relates to a process for fabricating the planar sensor described above, which comprises zirconium dioxide and aluminum oxide and is suitable for measuring the proportions of oxygen and combustible gases in the exhaust gases of internal combustion engines or furnaces. The process comprises casting a liquid ceramic tape-casting composition comprising organic additives, especially a volatile organic solvent, finely dispersed zirconium dioxide and optionally inorganic dopants, onto a flat substrate and generating a thin film in the process, drying the film and detaching it from the substrate, punching a plurality of equal-sized cards from the dried film, which approximately correspond to the dimensions of the eventual sensor applying onto the surface of a first card, by printing a platinum metal paste thereon, an electrode which extends at least as far as the central region of the card which is connected to the edge of the card via a printed conductor, applying onto this first surface at least one second card which in its central region has a cutout, applying onto this second card at least one third card which carries two platinum and platinum alloy electrodes extending at least as far as the central region of the card, which electrodes are applied by corresponding pastes being printed on and which are connected to the edge of the card via printed conductors, in such a manner that the surface having the platinum and platinum alloy electrodes faces away from the second card having the cutout in the central region, and firing this card structure oxidatively at from 1400° to 1600° C. the three cards sintering together to form a zirconium dioxide sensor having a planar structure.

The liquid ceramic tape-casting composition comprises, as organic additives, especially binders, dispersants, a volatile solvent (e.g. trichloroethylene/alcohol) and plasticizers. The substrate used for casting can be a steel plate, a mobile steel strip or a smooth plastic film, e.g. a polyester film. The thickness of the resulting film is approximately from 0.2 to 2 mm, preferably from 0.3 to 0.9 mm. A constant thickness of the thin film can be achieved by using a casting shoe. The film can also be dried continuously. The dimensions of the cards punched out shrink during ceramic firing, depending on the volume proportion of organic components, by from 10 to 30%, especially from 22 to 25%.

The invention is explained below in more detail by way of example with reference to the accompanying figures, without however being restricted to the concrete embodiment shown.

Figure 1:
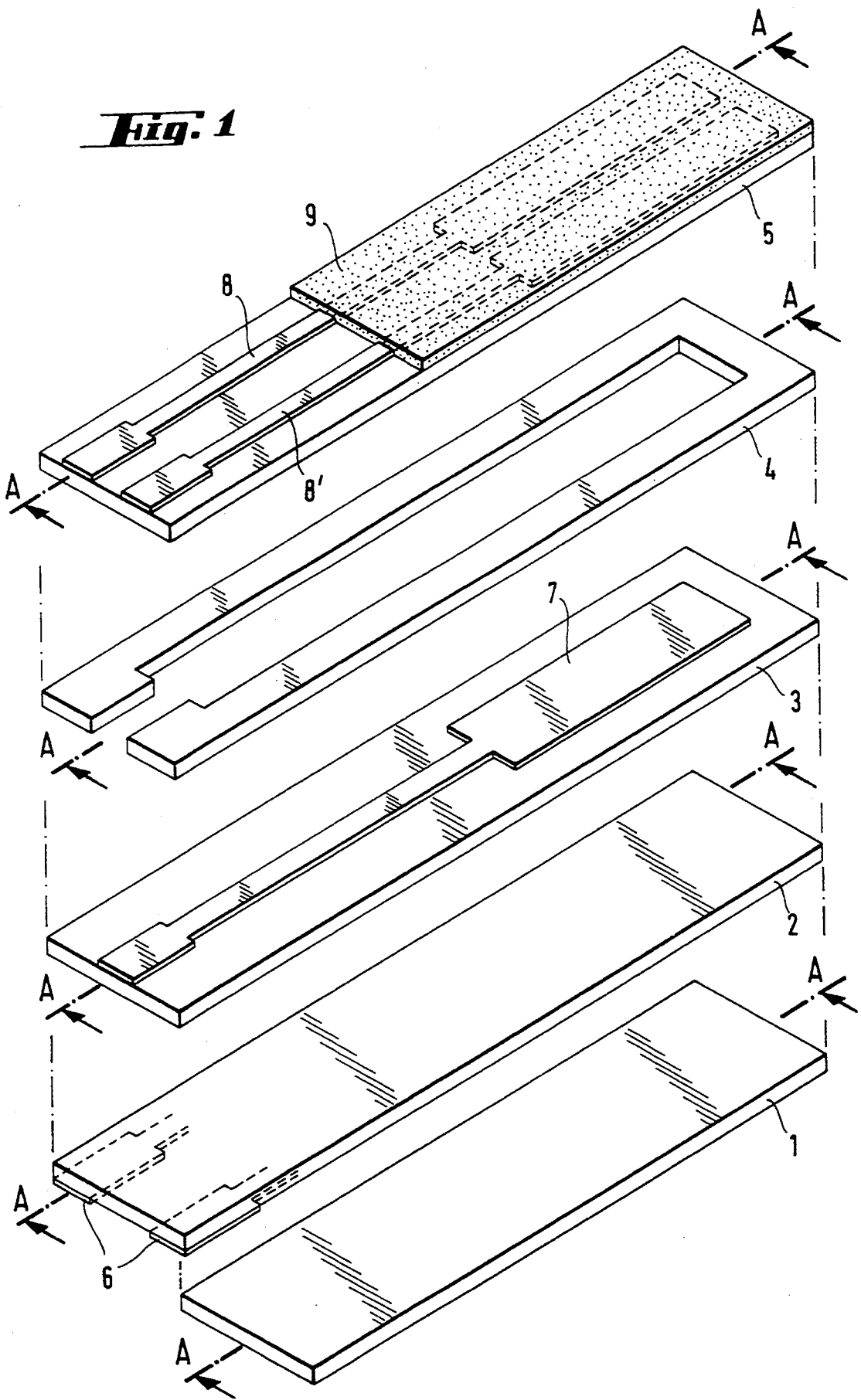
FIG. 1 shows a diagram of the layer structure of a sensor according to the invention.

Reference numbers are used in FIG. 1 to clarify the first aluminum oxide layer 1 and the second aluminum oxide layer 2, the electric heating resistor 6 being only just visible on the underside of the second aluminum oxide layer 2. Adjoining the second aluminum oxide layer 2 there is the first zirconium dioxide layer 3 which on its top side carries an electrode 7 made of platinum. The zirconium dioxide layer 4 having the central cutout then follows, and the termination is finally formed by the zirconium dioxide layer 5 which on its top side carries two electrodes 8 and 8', arranged parallel to one another, one made of platinum and one made of a platinum alloy, which are coated, in the region of the actual measuring surface, with a thin protective layer 9 made of mullite, spinel or porous zirconium dioxide.

Figure 2:
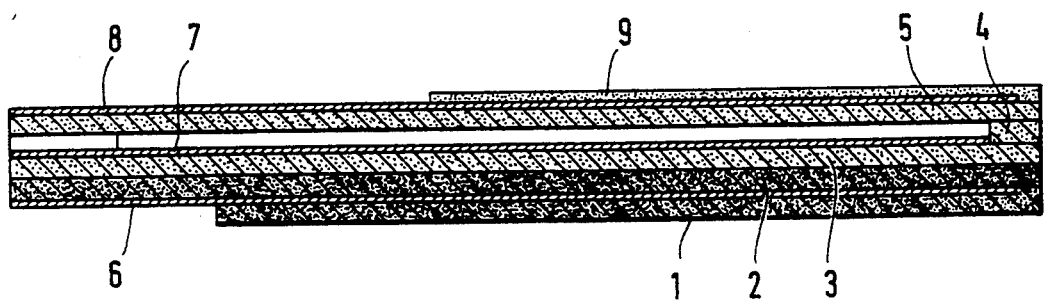
FIG. 2 shows a side view of a vertical section through a sensor of FIG. 1 along the line A—A.

In FIG. 2, identical reference numbers have the identical meaning as in FIG. 1.

Figure 3:
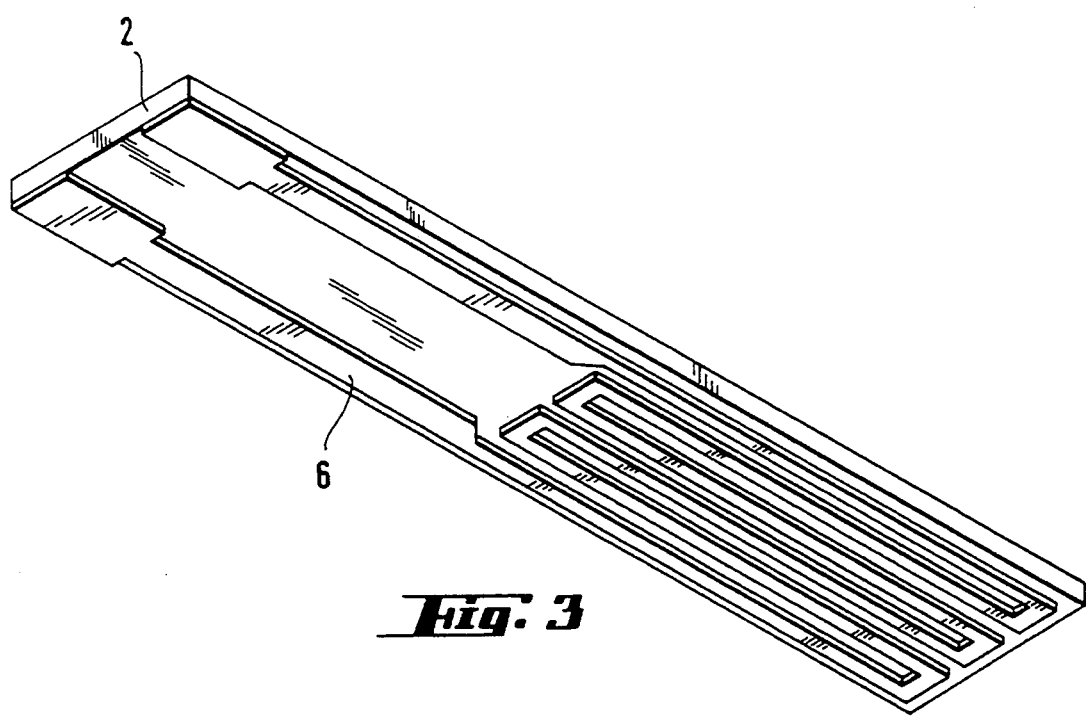
FIG. 3 shows the heating resistor, applied to aluminum oxide ceramic from FIG. 1, in a view from below.

FIG. 3 shows the second aluminum oxide layer 2 in a view from below, illustrating, in particular, how the electric heating resistor layer 6 extends like a meander over the underside of the layer 2.

We claim:

1. A planar sensor made of ceramic material, for measuring and detecting combustible gases and the oxygen content in furnaces or in exhaust gases of internal combustion engines, wherein the sensor has an at five-layered structure comprising a combination of three zirconium dioxide layers with two aluminum oxide layers, wherein a metallic heating resistor is embedded between two aluminum oxide layers, and wherein three zirconium dioxide layers are combined with two platinum electrodes and at least one further electrode made of a binary or ternary alloy of platinum with one or more compounds selected from the group consisting of gold, nickel, copper, rhodium, ruthenium, palladium and titanium, wherein said zirconium dioxide layers are arranged in such a way that, on a first layer, an electrode made of platinum is arranged which is applied as a paste comprising said platinum metal as a finely particulate powder together with an organic binder, and wherein, on the first layer with the electrode made of platinum, a second layer made of zirconium dioxide is arrange which has a central cutout with a connection to an external edge of said second layer, and wherein a termination is formed by a third layer made of zirconium dioxide which, on its top surface which faces way from the second layer having the cutout, carries two electrodes which are arranged in parallel and which are made of platinum and of a binary or ternary alloy of platinum with a compound selected from the group consisting of gold, nickel, copper, rhodium, ruthenium, palladium and titanium.

2. The sensor as claimed in claim 1, wherein the electrodes of the third zirconium dioxide layer are additionally coated with a protective layer.

3. The sensor as claimed in claim 1, wherein the platinum electrodes and platinum alloy electrodes on a third zirconium dioxide layer are applied as pastes which comprise platinum or a platinum alloy as a finely particulate powder together with organic binders.

4. The sensor as claimed in claim 3, wherein the platinum electrodes and platinum alloy electrodes are applied as a paste comprising platinum or a platinum alloy as a finely particulate powder together with an organic binder and a solvent.

5. The sensor as claimed in claim 1, wherein the zirconium dioxide composition additionally comprises one or more dopants selected from the group consisting of CaO, MgO, CeO and $Y_2O_3$, wherein the amount of the dopants is in the range from 3.5 to 14.0% by weight, based on the total amount of zirconium dioxide composition.

6. The sensor as claimed in claim 5, wherein the amount of the dopants is in the range from 5 to 10% by weight, based on total amount of zirconium dioxide composition.

7. The sensor as claimed in claim 1, wherein the individual zirconium dioxide layers have layer thicknesses which are different and are in a range of from 0.2 to 2.0 mm.

8. The sensor as claimed in claim 7, wherein the layer thicknesses of the individual zirconium dioxide layers are in the range from 0.5 to 1.1 mm.

9. The sensor as claimed in claim 8, wherein the layer thicknesses of the individual zirconium dioxide layers are in the range from 0.5 to 0.9 mm.

10. The sensor as claimed in claim 1, wherein the metallic heating resistor has a meandering construction.

11. The sensor as claimed in claim 10, wherein the metallic heating resistor is constructed of tungsten.

12. The sensor as claimed in claim 1, wherein said sensor is combined with a housing whose interior is subdivided into two chambers in a gas-tight manner by a ceramic element fixing the position of the sensor, a first chamber is in direct contact with combustion exhaust gases, and a second chamber is insulated from said combustion exhaust gases, wherein said sensor is arranged in the housing in such a way that said two electrodes disposed on said third zirconium dioxide layer are located in the first chamber in direct contact with said combustion exhaust gases, while a voltage pick-off takes place in said second chamber.

13. The sensor as claimed in claim 1, wherein said electrode made of platinum is applied on said first layer as a paste comprising said platinum metal as a finely particulate powder together with an organic binder and a solvent.

* * * * *